United States Patent
Ehrman et al.

(10) Patent No.: US 12,036,298 B2
(45) Date of Patent: *Jul. 16, 2024

(54) SKIN CARE COMPOSITION AND METHOD FOR TREATING POST-ACNE MARKS

(71) Applicant: The Procter & Gamble Company, Cincinnati, OH (US)

(72) Inventors: Matthew Clair Ehrman, Singapore (SG); Dissanayake Mudiyanselage Mahathma Bandara Dissanayake, Mason, OH (US); Joseph Michael Zukowski, Blue Ash, OH (US); Wan Ting Chung, Singapore (SG); Zhi Yan Chew, Cincinnati, OH (US); Shikhar Gupta, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/070,863

(22) Filed: Nov. 29, 2022

(65) Prior Publication Data
US 2023/0165779 A1 Jun. 1, 2023

Related U.S. Application Data

(60) Provisional application No. 63/283,737, filed on Nov. 29, 2021.

(51) Int. Cl.
| | |
|---|---|
| *A61K 8/365* | (2006.01) |
| *A61K 8/23* | (2006.01) |
| *A61K 8/34* | (2006.01) |
| *A61K 8/368* | (2006.01) |
| *A61K 8/42* | (2006.01) |
| *A61K 8/49* | (2006.01) |
| *A61K 8/60* | (2006.01) |
| *A61K 8/67* | (2006.01) |
| *A61Q 19/00* | (2006.01) |
| *A61Q 19/08* | (2006.01) |

(52) U.S. Cl.
CPC .............. *A61K 8/365* (2013.01); *A61K 8/23* (2013.01); *A61K 8/345* (2013.01); *A61K 8/368* (2013.01); *A61K 8/42* (2013.01); *A61K 8/4926* (2013.01); *A61K 8/60* (2013.01); *A61K 8/675* (2013.01); *A61Q 19/00* (2013.01); *A61Q 19/08* (2013.01); *A61K 2800/48* (2013.01); *A61K 2800/522* (2013.01); *A61K 2800/805* (2013.01)

(58) Field of Classification Search
CPC .......... A61K 8/365; A61K 8/23; A61K 8/345; A61K 8/368; A61K 8/42; A61K 8/4926; A61K 8/60; A61K 8/675; A61K 2800/48; A61K 2800/522; A61K 2800/805; A61K 8/44; A61K 8/8152; A61Q 19/00; A61Q 19/08
See application file for complete search history.

(56) References Cited

U.S. PATENT DOCUMENTS

| | | | |
|---|---|---|---|
| 6,632,444 B1 | 10/2003 | Zhou et al. | |
| 7,179,841 B2 | 2/2007 | Zielinski et al. | |
| 2005/0100517 A1 | 5/2005 | Sanzgiri et al. | |
| 2010/0189669 A1 | 7/2010 | Hakozaki | |
| 2014/0107046 A1 | 4/2014 | Pan et al. | |
| 2014/0161849 A1 | 6/2014 | Bickford | |
| 2016/0101029 A1 | 4/2016 | Serrano Sanmiguel et al. | |
| 2016/0151270 A1 | 6/2016 | Brooks et al. | |
| 2018/0116936 A1 | 5/2018 | Pan et al. | |
| 2021/0346275 A1* | 11/2021 | Carle | A61Q 19/02 |
| 2023/0021127 A1* | 1/2023 | Maruyama | A61K 8/73 |
| 2023/0046148 A1* | 2/2023 | Stebbins | A61K 8/347 |
| 2023/0165767 A1 | 6/2023 | Ehrman et al. | |

FOREIGN PATENT DOCUMENTS

| | | |
|---|---|---|
| CN | 106309156 A | 1/2017 |
| CN | 110638692 A | 1/2020 |
| CN | 112022766 A | 12/2020 |
| EP | 2906037 B1 | 8/2018 |
| WO | 0107004 A1 | 2/2001 |
| WO | 2005044214 A1 | 5/2005 |
| WO | 2008052674 A1 | 5/2008 |
| WO | 2011042073 A2 | 4/2011 |
| WO | 2013016257 A1 | 1/2013 |
| WO | 2019108450 A1 | 6/2019 |
| WO | 2020010036 A1 | 1/2020 |
| WO | 2020122088 A1 | 6/2020 |
| WO | 2021125070 A1 | 6/2021 |
| WO | 2021232040 A1 | 11/2021 |

OTHER PUBLICATIONS

Banish (2021, banish.com/blogs/ article/how-ferulic-acid-benefits-skin (Year: 2021).*
All Office Actions; U.S. Appl. No. 18/070,570, filed Nov. 29, 2022.
All Office Actions; U.S. Appl. No. 18/070,575, filed Nov. 29, 2022.
Unpublished U.S. Appl. No. 18/070,570, filed Nov. 29, 2022, to Matthew Clair Ehrman et al.
Unpublished U.S. Appl. No. 18/070,575, filed Nov. 29, 2022, to Matthew Clair Ehrman et al.
PCT Search Report and Written Opinion for PCT/US2022/080559 dated Apr. 6, 2023, 15 pages.

(Continued)

*Primary Examiner* — Lezah Roberts
*Assistant Examiner* — Abdulrahman Abbas
(74) *Attorney, Agent, or Firm* — Alexandra S. Anoff

(57) ABSTRACT

A method for reducing the appearance of post-acne marks, lightening dark spots and discoloration, fading post-acne marks faster and/or preventing appearance of new post-acne marks by applying a skin care composition. The skin care composition contains a vitamin $B_3$ compound, hydroxycinnamic acid, and water at a pH of less than 5.0.

18 Claims, 4 Drawing Sheets

(56) References Cited

OTHER PUBLICATIONS

Database GNPD [Online] Mintel; anonymous: "Acne Eliminating Gel", Jul. 31, 2020, 6 pages, XP093033428,Database accession No. 7945189.
Database GNPD [Online] Mintel; anonymous: "Advanced Brighten Treatment Serum", Aug. 17, 2020, 6 pages, XP093033429,Database accession No. 7974155.
Database GNPD [Online] Mintel; anonymous: "Haute C Bright Serum Concentrate", Jul. 6, 2020, 7 pages, XP093033427,Database accession No. 7935589.
Nair Nirmala et al, "26415 Regulation of postinflammatory hyperpigmentation by niacinamide through potential modulation of the protease inhibitor, SERPINB3", Journal of the American Academy of Dermatology, Mosby, Inc, US, vol. 85, No. 3, Aug. 7, 2021, 1 page, XP086725903, ISSN: 0190-9622.
All Office Actions; U.S. Appl. No. 18/070,572, filed Nov. 29, 2022.
Banish (2021, Ferulic Acid and What it does for your skin, URL Link-banish.com/blogs/ article/how-ferulic-acid-benefits-skin (Year: 2021), 3 pgs.

* cited by examiner

SKIN CARE COMPOSITION AND METHOD FOR TREATING POST-ACNE MARKS

FIELD

The present disclosure generally relates to low-pH skin care compositions containing stable, solubilized hydroxycinnamic acid (HCA) and niacinamide that reduce the appearance of post-acne marks. More specifically, the present disclosure relates to low-pH skin care compositions that contain stable HCA and a solubilizing amount of a polar emollient and a suitable co-solvent.

BACKGROUND OF THE INVENTION

Consumers feel most healthy and attractive when their skin appears soft, smooth, even, moisturized, and vibrant. Numerous studies have shown facial skin color uniformity plays an important role in perception of health, beauty, and attractiveness. In particular, skin challenges that cause deviations and non-uniformity from one's normal skin color poses psychological stress to those affected. Acne is a common skin disorder that affects a large majority of younger consumers and many people in the general population.

Patients with acne have been found to have lower self-esteem, depression, anxiety, feelings of social isolation, impaired relationships with others, and weakened ability to focus on work and school. Unfortunately, in addition to acne itself, a common complication of acne is residual postinflammatory hyperpigmentation (PIH) and/or postinflammatory erythema (PIE), which causes further psychological and social distress in affected patients. These "marks" caused by acne are a frequent complaint from consumers and are a top skin care concern, especially among younger consumers.

Post-acne marks are generally slow to heal, and darker skin tones are more prone to these marks because of the higher levels of melanin in the skin. Today, some of the most efficient treatments for post-acne marks require a trip to the dermatologist for prescription-strength products, such as prescription-strength retinoids, or in-office treatments such as a chemical peal or high intensity light therapies.

Therefore, there is a need for a skin care composition that can accelerate the healing of post-acne marks without a trip to the dermatologist.

SUMMARY OF THE INVENTION

A method of reducing the appearance of post-acne marks comprising: (a) identifying a target portion of skin comprising a post-acne mark; (b) applying an effective amount of a skin care composition to the target portion of skin over the course of a treatment period; wherein the skin care composition comprises: (i) about 0.1% to about 10% of a vitamin $B_3$ compound; (ii) about 0.1% to about 10% of a hydroxycinnamic acid; (iii) water; wherein a pH of the composition is 5.0 or less.

A method of lightening the appearance of dark spots and discoloration comprising: (a) identifying a target portion of skin comprising a post-acne mark; (b) applying an effective amount of a skin care composition to the target portion of skin over the course of a treatment period; wherein the skin care composition comprises: (i) niacinamide; (ii) coumaric acid; (iii) isopropyl lauroyl sarcosinate; (iv) pentylene glycol; wherein the composition comprises a pH of less than 5.0, a viscosity of about 1 cP to about 15,000 cP at 25° C., and is substantially free of coumaric acid crystals.

A method of fading post-acne marks faster and/or preventing appearance of new post-acne marks comprising (a) identifying a target portion of skin comprising a post-acne mark; (b) applying an effective amount of a skin care composition to the target portion of skin over the course of a treatment period; wherein the skin care composition comprises: (i) a vitamin $B_3$ compound; (ii) a hydroxycinnamic acid; (iii) a polar emollient; (iv) a co-solvent with a Hansen solubility parameter distance of less than 15 from the hydroxycinnamic acid; and (v) water; wherein the pH of the composition is less than 5.0 and the composition exhibits less than 25% HCA degradation according to the HPLC Method.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1A:
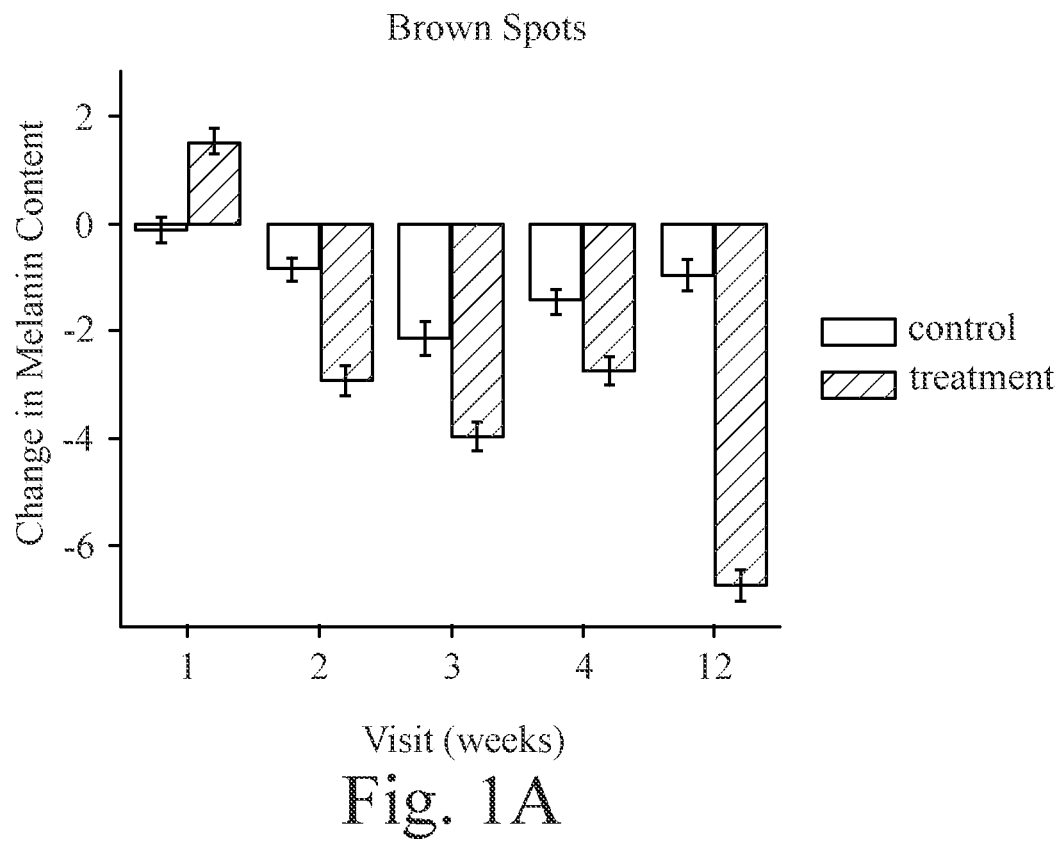
FIG. 1A shows the change in melanin content in brown spots over 12 weeks for a Treatment Product and a Control Product.

Post-acne marks can be persistent and there are few over-the-counter remedies that are effective in returning the skin to its original uniformity. Post-acne marks are hypothesized to follow a dynamic path as follows. When the skin is subjected to an insult (e.g., acne including comedones, wounds, insect bites), local inflammation starts, and one or more red spots are often formed. The redness and inflammation are generally attributed to the chromophore hemoglobin. With time, the amount of hemoglobin in red spots can change, which alters the spots' appearance. In some cases, increased melanin production is also observed in these red spots. This increase in melanin tends to cause a darkening of the spots' appearance. These spots can naturally heal with time and therefore, hemoglobin and/or melanin in these spots is expected to reduce over time. However, sometimes, especially in more severe spots, the spots may stay on the skin for a longer period.

It was found that a composition with hydroxycinnamic acids (HCAs) and niacinamide at a low pH can decrease the melanin and hemoglobin in persistent post-acne spots, as described in the clinical study, hereafter, and the results are shown in the Figures.

The methods and compositions described herein can be useful on post-acne marks and other blemishes, stubborn marks, blemish marks, postinflammatory hyperpigmentation, and postinflammatory erythema. The term "marks" and "spots" can be used interchangeably.

It was recently discovered that low-pH compositions can improve the efficacy of certain skin care actives such as niacinamide (see, U.S. Pat. No. 10,874,600). However, it was challenging to formulate a low-pH composition with both niacinamide and HCAs because HCAs tend to exhibit undesirable solubility and/or stability characteristics in conventional aqueous skin care products and the solubility problems are generally exacerbated at low pH.

In order to increase the solubility of the HCA, some formulators add the HCA to the oil phase of the composition (i.e., in the case of an emulsion) or encapsulate the HCA. But these approaches can also be problematic. For example, adding a hydroxycinnamic acid to the oil phase can undesirably affect the sensory profile of the composition due to the introduction of oils and additional emulsifiers to the composition. And encapsulation can reduce the amount of hydroxycinnamic acid in the composition due to encapsulate loading limits.

Surprisingly, it was found that the stability and/or solubility characteristics of certain HCA compounds can be improved in a low-pH aqueous composition by formulating the composition with a suitable combination of polar emollient and glycol co-solvent. In particular, certain combinations of HCA, polar emollient and a co-solvent with a Hansen solubility parameter distance of less than 15 from the HCA can act synergistically to combat the undesirable stability and/or solubility effects of the HCA in an aqueous skin care composition.

Definitions

As used herein, "about" modifies a particular value by referring to a range equal to plus or minus twenty percent (+/−20%) or less (e.g., less than 15%, 10%, or even less than 5%) of the stated value.

As used herein, "apply" or "application," as used in reference to a composition, means to apply or spread the compositions of the present invention onto a human skin surface such as the epidermis.

As used herein, "cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration, food additives, and materials used in non-cosmetic consumer products including over-the-counter medications.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein. In a specific example, an effective amount of a vitamin $B_3$ compound is an amount sufficient to improve the health and/or appearance of psoriatic skin during a treatment period. In some instances, an effective amount may be demonstrated using ex vivo and/or in vitro methods.

As used herein, "hydroxycinnamic acid" (HCA) refers to a class of aromatic acids or phenylpropanoids having a C6-C3 skeleton that are hydroxy derivatives of cinnamic acid. Some non-limiting examples of HCA are caffeic acid, cichoric acid, cinnamic acid, chlorogenic acid, diferulic acids, coumaric acids (p-, o-, and m-isomers), ferulic acid, sinapinic acid, sinapic acid, and α-cyano-4-hydroxycinnamic acid.

As used herein, "improve the appearance of" means providing a measurable, desirable change or benefit in skin appearance, which may be quantified, for example, by a decrease in redness, inflammation, and/or plaque scales.

As used herein, "low-pH" means a pH of less than 5.0 (e.g., 1.5 to 4.9, 2.0 to 4.5, 2.5 to 4.0, or 3.5 to 4.0). A suitable method of determining the pH of a composition is described in more detail below.

As used herein, "neutral pH" means a pH of 5.0 to 8.0.

As used herein, "safe and effective amount" means an effective amount of an ingredient that is low enough to avoid serious side effects (within the scope of sound medical judgment).

As used herein, "skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin; preventing damage to skin via antioxidant approaches, including UV A and UV B induced damage, preventing formation of comedomes, balancing the skin microbiome or preventing acne.

As used herein, "skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

As used herein, "skin care composition" means a composition that includes a skin care active and regulates and/or improves skin condition.

As used herein, "treatment period," means the length of time and/or frequency that a material or composition is applied to a target skin surface.

All percentages are by weight of the cosmetic composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All weights as they pertain to listed ingredients are based on the active level and do not include carriers or by-products that may be included in commercially available materials, unless otherwise specified. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

Compositions

The skin care compositions described herein are low-pH compositions intended for topical application to human skin to improve the appearance, health, and/or function of skin. The present compositions may be used for non-therapeutic (i.e., cosmetic) treatment of a variety of skin conditions. In particular, the compositions can be used to reduce the appearance of post-acne marks.

The low-pH skin care compositions herein include a safe and effective amount of hydroxycinnamic acid (e.g., p-coumaric acid a.k.a. 4-HCA or p-HCA), a polar emollient and a suitable co-solvent with a Hansen solubility parameter distance of less than 15 from the HCA. The compositions herein may also include a vitamin $B_3$ compound such as niacinamide and/or one or more other optional skin care actives. The composition may optionally include a silicone emulsifier, a polymer thickener that can tolerate low-pH environments, a low molecular weight silicone fluid, an acid-salt pH-buffering system (e.g., a lactic acid/sodium lactate buffering system), and/or other ingredients commonly found in topical skin care compositions. It is believed, without being limited by theory, that the combinations of ingredients disclosed herein provides a stable and efficacious skin care composition that has good feel properties and is gentle on skin.

The compositions herein are formulated to provide improved HCA solubility in a low-pH environment. In an aqueous, low-pH skin care composition, HCA has a tendency to precipitate out of the composition and form crystals (HCA crystals), which can undesirably affect the look, feel, and/or efficacy of the composition. Conventional low-pH compositions often contain HCA crystals. However, the low-pH compositions herein contain a polar emollient and a co-solvent with a Hansen solubility parameter distance of less than 15 from the HCA. This combination of ingredients is specifically tailored to solubilize the HCA in the low-pH aqueous composition and inhibit HCA crystallization/precipitation. Thus, the compositions herein can be free of HCA crystals. A suitable method for measuring and/or characterizing the presence of HCA crystals in a composition is described in more detail below.

The low-pH compositions herein are also formulated to provide improved HCA stability. HCAs are relatively good antioxidant materials, and thus tend to be oxidized and/or degrade over time, which can result in a skin care composition that exhibits an undesirable color change (e.g., yellowing), an undesirable odor, and/or reduced efficacy. Formulating at a lower pH can improve HCA stability by reducing the rate at which it is oxidized, but it may be desirable, in some aspects, to include an antioxidant in the low-pH composition to help further reduce oxidation and/or degradation of the HCA.

The low-pH skin care compositions herein can be made by mixing the ingredients with a dermatologically acceptable carrier using conventional methods known to those skilled in the art. The compositions may be provided in various product forms such as solutions, suspensions, lotions, creams, gels, toners, sticks, sprays, aerosols, ointments, cleansing liquid washes and solid bars, pastes, foams, mousses, shaving creams, wipes, strips, patches, electric-powered patches, hydrogels, film-forming products, facial and skin masks (with and without insoluble sheet), and the like. The composition form may follow from the particular dermatologically acceptable carrier chosen.

In some instances, the low-pH skin care composition herein may be in the form of an essence. An essence is a form of topical skin care composition in a relatively concentrated formula that typically has a lower viscosity than a conventional cream- or lotion-type skin care composition. An essence may be provided in the form of a low viscosity fluid that is marketed to specifically target a particular skin condition and/or be used in the first step of a skin care regimen. The skin care essence products herein can have a dynamic viscosity of 1 centipoise (cP) to 15,000 cP at 25° C. (e.g., 50 cP to 10,000 cP or 100 cP to 7,500 cP, 200 cp to 5,000 cp, or 300 cp to 2,500 cp). A method of determining the viscosity of the low-pH compositions is described in more detail in the Methods section below.

Hydroxycinnamic Acid

The low-pH skin care compositions herein include a safe and effective amount of an HCA. The HCA may be present in the composition at 0.1% to 10% (e.g., 0.5% to 5% or 1% to 4%). Hydroxycinnamic acids are generally recognized as antioxidant phenolic compounds, which can be found in plants, mainly as a component of cell walls. See, H. K. Kuzaki et al., J. Agric. Food Chem., 50, 2161-68 (2002). In some aspects, it may be desirable to select coumaric acid for use in the low-pH composition, especially p-coumaric acid (a.k.a. 4-HCA). 4-HCA has the formula:

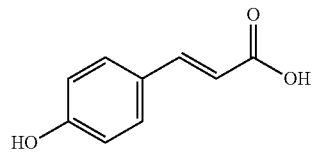

A particularly suitable example of an HCA material suitable for use herein is LIPOBRITE available from Vantage Personal Care.

Low-pH Solubilizer

The compositions herein include one or more solubilizers and/or co-solvents to help solubilize the HCA. HCA compounds generally exhibit especially poor solubility in low-pH aqueous composition, such as the low-pH compositions described herein. For example, p-coumaric acid has a solubility of approximately 345 mg/mL in water at pH 7.0 and 20° C. and a solubility of 4 mg/mL in water at pH 3.0 and 20° C. Without being limited by theory, it is believed that the decreased solubility of an HCA at lower pH is due to reduced ability of the HCA to undergo the acid dissociation that forms the conjugate base species observed at higher pH levels. At pH 7, p-coumaric acid exists at approximately 99.6% in its base form; whereas at pH 3, the conjugate base form is only present at approximately 13.4%. As a result of its relatively poor solubility, HCAs can form crystals in an aqueous, low-pH skin care composition. The HCA crystals may impart an undesirable feel to the composition during use (e.g., a rough or grainy feel). HCA crystal formation may also lead to a decrease in the efficacy of the HCA and/or other ingredients in the composition, and/or create an undesirable consumer perception of the skin care composition or manufacturer (e.g., poor quality).

In order to avoid the formation of HCA crystals in the present low-pH compositions, the HCA should have a solubility greater than the intrinsic solubility limit of the composition. For example, a 1.0% HCA formula at pH of 3.8 with water at approximately 75% has a concentration of 13.3 mg/ml at 20° C., whereas the intrinsic solubility is 6.8 mg/mL. In this example the HCA would likely crystalize. Hydroxycinnamic acids have been shown to complex and co-crystalize with certain materials, and so the intrinsic solubility limit alone may not fully predict crystallization stability. See, Bevill, et al., Polymorphic Cocrystals of Nutraceutical Compound p-Coumaric Acid with Nicotinamide: Characterization, Relative Solid-State Stability, and Conversion to Alternate Stoichiometries, Cryst. Growth Des. 2014, 14, 3, 1438-1448; 2014.

It has now been found that certain combinations of polar emollients (e.g., isopropyl lauroyl sarcosinate) and co-solvents with a Hansen solubility parameter distance of less than 15 from the HCA (e.g., certain glycols) can greatly improve the solubility of HCA in a low-pH aqueous composition. Emollients are substances that tend to soften and moisturize skin by forming an oily layer on top of the skin that traps water in the skin. Some common examples of emollients include petrolatum, lanolin, mineral oil and dimethicone. Polar emollients are useful herein for solubilizing HCA, but polar emollients can also destabilize an oil-in-water emulsion, which is a common product form for skin care composition. Thus, it can be important to tailor the type and amount of polar emollient in the composition to help solubilize the HCA in the composition, but avoid emulsion instability. Not all polar emollients will work with all HCAs.

In some aspects, the low-pH composition herein may include 0.5% to 10% of a polar emollient (e.g., 1% to 5% ELDEW SL-205 brand isopropyl lauroyl sarcosinate available from Ajinomoto OmniChem), which has been found to solubilize p-coumaric acid, especially when combined with a suitable glycol. Some non-limiting examples of polar emollients that may be suitable for use herein are amino acid ester derivatives (e.g., lauroyl arginine, arginine lauroyl glutamate, phytosteryl/octyldodecyl lauroyl glutamate, and dihexyldecyl lauroyl glutamate) and hydrocarbon esters (e.g., cyclohexylglycerin and isopropyl myristate).

The compositions herein also include a co-solvent with a Hansen solubility parameter distance of less than 15 from the HCA that acts in combination with the polar emollient to help solubilize the HCA. Hansen solubility parameter distance is described in *Hansen solubility parameters: a user's handbook*, CRC press, 2007 and can be calculated using the following equation:

$$\sqrt{4*(\delta_{D2}-\delta_{D1})^2+(\delta_{P2}-\delta_{P1})^2+(\delta_{H2}-\delta_{H1})^2}$$

Where:
$\delta_D$=Hansen dispersion,
$\delta_P$=Hansen polarity, and
$\delta_H$=Hansen hydrogen bonding.

Co-solvents suitable for use herein include short chain dihydric alcohols (e.g., glycols). However, when a glycol is selected as the co-solvent, it can be important to limit the amount of glycol in the low-pH composition to less than 25% (e.g., less than 20%, 17%, 15%, or even less than 10%), but generally greater than 1%, to avoid undesirable feel characteristics (e.g., sticky feeling or greasy feeling). Some non-limiting examples of glycols that may be suitable for use herein are propylene glycol, dipropylene glycol, butylene glycol, pentylene glycol, hexylene glycol, ethoxydiglycol, and C2-C6 polyethene glycols (e.g., PEG-3, PEG-4, PEG-4 methyl ether), and combinations thereof.

In some aspects, the polar emollient and co-solvent may be present in the low-pH composition at a weight ratio of polar emollient to co-solvent of 1:3 to 3:1 (e.g., 2:3, 1:1, or 2:1). In some aspects, the HCA may be premixed with the co-solvent and/or polar emollient and, optionally, one or more other ingredients and then added to the composition.

Vitamin $B_3$ Compound

The present composition may include a safe and effective amount of a vitamin $B_3$ compound for regulating a variety of skin condition, for example, as described in U.S. Pat. No. 5,939,082. The compositions herein may contain 0.1% to 10%, by weight, of the vitamin $B_3$ compound, based on the weight or volume of the composition (e.g., 0.5% to 5% or 1% to 4%).

As used herein, "vitamin $B_3$ compound" means a compound having the formula:

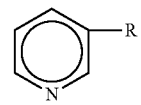

Where:
R is $CONH_2$ (i.e., niacinamide), $COOH$ (i.e., nicotinic acid) or $CH_2OH$ (i.e., nicotinyl alcohol); derivatives thereof; and salts of any of the foregoing. Exemplary derivatives of vitamin B3 compounds include nicotinic acid esters, including non-vasodilating esters of nicotinic acid (e.g., tocopheryl nicotinate, myristyl nicotinate) nicotinamide riboside, nicotinyl amino acids, nicotinyl alcohol esters of carboxylic acids, nicotinic acid N-oxide, and niacinamide N-oxide. In some instances, vitamin $B_3$ compounds such as niacinamide may have improved efficacy at lower pH, for example, as described in U.S. Publication No. 2020/0009123.

In some instances, it may be desirable for the ring nitrogen of the vitamin $B_3$ compound to be "uncomplexed" (e.g., chemically unbound and/or unhindered) in the composition and/or prior to application to a target skin surface. For example, the compositions herein may be free of or substantially free of (i.e., less than 3%, 2%, 1% or even less than 0.5%) a salt or complex of a vitamin $B_3$ compound. Exemplary approaches to minimizing or preventing the formation of undesirable salts and/or complexes include omission of materials that form substantially irreversible or other undesirable complexes with the vitamin $B_3$ compound in the composition, pH adjustment, ionic strength adjustment, the use of surfactants, and practicing formulation processes wherein the vitamin $B_3$ compound and materials which complex therewith are in different phases.

Antioxidant

The low-pH composition herein may include an antioxidant to combat HCA oxidation and/or degradation. The antioxidant, when included, may be present at 0.001% to 3% (e.g., 0.01% to 2%, 0.05% to 1%, or 0.1% to 0.5%). Some non-limiting examples of antioxidants that may be suitable for use herein are sodium sulfite, sodium bisulfite sodium metabisulfite, and butylated hydroxytoluene.

Low-pH Acid Buffering System

When providing a low-pH composition for topical application to skin, it can be important to include a buffering system to help maintain the pH of the composition for a period of time after it is applied to the skin (e.g., up to 5 minutes or more). On average, human skin pH typically ranges from about 5.0 to 6.0. To maintain this pH, human skin has evolved a natural buffering system that resists changes to pH. Thus, when a low-pH composition is applied to the skin, the skin's natural buffering system will try to adjust the pH of the composition to match the natural pH of the skin. Without the addition of the buffering agent, the low-pH composition may not be able to provide the desired skin care benefit. Accordingly, the compositions herein may include a low-pH acid buffering system.

The buffering agent may be selected according to the acid(s) that is used to lower the pH of the low-pH compositions herein. For example, lactic acid and gluconic acid may be used, individually or in combination, to lower the pH of the composition because they are generally considered gentler on skin (i.e., lower risk of irritation) compared to other alpha hydroxy acids. In this example, sodium lactate and/or sodium gluconate would then be selected as the corresponding salt buffering agent to provide the acid/salt pH buffer system. The buffering agent may be present in the low-pH composition at 0.25% to 4% (e.g., 0.5% to 3%, 0.75% to 2% or 1% to 1.75%). A non-limiting example of a suitable low-pH buffer system for use herein is disclosed in co-pending U.S. Ser. No. 16/891,491. Of course, it is to be appreciated that the present composition may optionally include other pH buffers known for use in skin care compositions.

Thickener

The composition may include a polymer thickener that can tolerate a low-pH, electrolytic environment. That is, the thickener will not lose its ability to thicken or stabilize the composition at low-pH in the presence of an acid-salt buffering system. Some conventional neutralized thickeners are known to degrade and/or lose the ability to suitably thicken a composition at lower pH and/or in the presence of an acid-salt buffer (e.g., sodium lactate). For example, some neutralized thickeners degrade in a low-pH environment. On the other hand, fatty alcohol thickeners such as cetyl alcohols and stearyl alcohols are generally stable at low pH, but tend to impart an undesirable cloudiness or opacity to the composition when it is in the form of an essence, serum, or the like. It has also been found that certain anionic polymeric thickeners can provide suitable tolerance to low-pH environments but cannot tolerate buffer systems due to combination of acid and salt. Thus, in some instances, the low-pH composition described herein may be free or substantially free of neutralized thickeners, fatty alcohol thickeners, and anionic thickeners. The thickener may be present at 0.0001% to 25% (e.g., 0.001% to 20%, 0.01% to 10%, 0.5% to 7%, or 1% or 5%) by weight of the composition.

Other nonlimiting examples of thickeners or water structuring agents that may be used alone or in combination herein include natural or synthetic gums, polysaccharides, carboxylic acid polymers, polyacrylamide polymers, sulfonated polymers, and copolymers of these. Further examples include modified gums, celluloses, and superabsorbent polymers. The term "superabsorbent polymer" is understood to mean a polymer which is capable, in its dry state, of spontaneously absorbing at least 20 times its own weight of aqueous fluid, in particular of water and especially of distilled water. Suitable polysaccharides include alkyl hydroxyalkyl cellulose ethers, such as hydroxypropylmethylcellulose stearoxy ether. This material is sold under the tradename of SANGELOSE 60L and 90L from Daido Chemical Corp. Another suitable polysaccharide includes hydrophobically modified starch, such as Potato modified starch. This material is sold under the tradename of STRUCTURE SOLANACE by Nouryon. Another polymer includes crosslinked polymers, the monomers of which are at least partially composed of acryloyldimethyltaurate monomers, such as, for example sodium polyacryloyldimethyl taurate, sold under the tradename of ARISTOFLEX SILK, from Clariant.

It has now been found that certain anionic polymeric thickeners can provide suitable tolerance to low-pH environments and the desired feel and opacity properties to the composition. Thus, a particularly suitable example of an anionic thickener is polyacrylate crosspolymer-6, which is commercially available as SEPIMAX ZEN from Seppic, France.

Low Molecular Weight Silicone Fluid

In some instances, an anionic polymeric thickener may impart an undesirable tacky feel when the low-pH composition is applied to a target portion of skin. It has been found that the addition of a low molecular weight silicone fluid can reduce or prevent this tacky feel. The molecular weight of a silicone fluid depends on the length of its silicone polymer chain(s), which is also directly proportional to the viscosity of the silicone fluid. Thus, the low molecular weight silicone fluids suitable for use in the present low-pH composition have a kinematic viscosity of 100 cSt or less at 25° C. (e.g., 1 cSt to 90 cSt, 5 cSt to 50 cSt, or even 10 cSt to 30 cSt). Kinematic viscosity is a common method of classifying silicone fluids and can be obtained from the supplier of the material. A particularly suitable example of a low molecular weight silicone fluid is 5 cSt dimethicone fluid. As used herein, "dimethicone" means a polydimethylsiloxane compound having the formula:

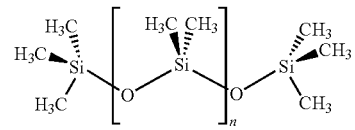

Dermatologically Acceptable Carrier

The low-pH compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion. The emulsion may have a continuous aqueous phase (e.g., an oil-in-water or water-in-oil-in-water emulsion) or a continuous oil phase (e.g., water-in-oil or oil-in-water-in-oil emulsion). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable, hydrophilic diluents. As used herein, "diluent" includes materials in which the vitamin $B_3$ compound can be dispersed, dissolved, or otherwise incorporated. Hydrophilic diluents include water, organic hydrophilic diluents such as lower monovalent alcohols (e.g., $C_1$-$C_4$) and low molecular weight glycols and polyols, including propylene glycol, polyethylene glycol (e.g., molecular weight of 200 to 600 g/mole), polypropylene glycol (e.g., molecular weight of 425 to 2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof Emulsifier When the low-pH composition herein is in the form of an emulsion (e.g., oil-in-water emulsion), it may be desirable to include an emulsifier to stabilize the emulsion (i.e., prevent the emulsion from phase separating). The emulsifier may be present in the composition at 0.01% to 10% (e.g., 0.05% to 5% or 0.1% to 2%). The emulsifiers may be nonionic, anionic or cationic. In some instances, the emulsifier may be a silicone emulsifier. Some non-limiting examples of emulsifiers that may be suitable for use herein are disclosed in U.S. Pat. Nos. 3,755,560; 4,421,769; and McCutcheon's Detergents and Emulsifiers, North American Edition, pages 317-324 (1986).

Some other non-limiting examples of emulsifiers that may be suitable for use herein include ethers of polyglycols and of fatty alcohols, esters of polyglycols and of fatty acids, ethers of polyglycols and of fatty alcohols which are glycosylated, esters of polyglycols and of fatty acids which are glycosylated, ethers of C12-30 alcohols and of glycerol or of polyglycerol, esters of C12-30 fatty acids and of glycerol or of polyglycerol, ethers of oxyalkylene-modified C12-30 alcohols and of glycerol or polyglycerol, ethers of C1-230 fatty alcohols comprising and of sucrose or of glucose, esters of sucrose and of C1230 fatty acids, esters of pentaerythritol and of C12-30 fatty acids, esters of sorbitol and/or of sorbitan and of C12 30 fatty acids, ethers of sorbitol and/or of sorbitan and of alkoxylated sorbitan, ethers of polyglycols and of cholesterol, esters of C12-30 fatty acids and of alkoxylated ethers of sorbitol and/or sorbitan, and combinations thereof. A particularly useful class of emulsifiers is polyethylene glycol ethers of lauryl alcohol such as laureth-1 through laureth-50 (e.g., laureth-4). Still other examples of emulsifiers include ethers of glycerol, polyglycerol, sucrose, glucose, or sorbitol; esters of glycerol, polyglycerol, sucrose, glucose, or sorbitol; and mixtures thereof. Other particularly useful classes of emulsifiers are the alkyl esters of sorbitol and sorbitol anhydrides such as polysorbate 20, polysorbate 21, and polysorbate 40.

In some aspects, it may be desirable to include a linear or branched silicone emulsifier in the low-pH composition. Particularly useful silicone emulsifiers may include polyether modified silicones such as KF-6011, KF-6012, KF-6013, KF-6015, KF-6015, KF-6017, KF-6043, KF-6028, and KF-6038 and polyglycerolated linear or branched siloxane emulsifiers such as KF-6100, KF-6104, and KF-6105; all from Shin-Etsu. A particular suitable emulsifier for use herein is PEG-11 methyl ether dimethicone, which is available from Shin-Etsu as KF-6011. It was discovered that the PEG-11 methyl ether dimethicone emulsifier further reduced the tacky feel of the anionic polymer thickener, thereby improving the overall feel of the low-pH composition. The emulsifier may be present at an amount of 0.1% to 10% (e.g., 1% to 5%, or 2%-4%).

Other Optional Ingredients

The present composition may optionally include one or more additional ingredients commonly used in cosmetic compositions (e.g., colorants, skin care actives, anti-inflammatory agents, sunscreen agents, emulsifiers, buffers, rheology modifiers, combinations of these and the like), provided that the additional ingredients do not undesirably alter the skin health or appearance benefits provided by the present compositions. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, antioxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

When including optional ingredients in the compositions herein, it may be desirable to select ingredients that do not form complexes or otherwise undesirably interact with other ingredients in the composition at low-pH, especially pH sensitive ingredients like niacinamide, salicylates and peptides. In some instances, it may be desirable to select skin care actives that function via different biological pathways so that the actives do not interfere with one another, which could reduce the efficacy of both agents. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

Method of Use the skin care compositions are formulated for topical application to the skin. The method of using the skin care composition involves identifying a target portion of skin on a person in need of treatment or where treatment is desired (e.g., portions of skin exhibiting post-acne marks) and applying an effective amount of the composition to the target portion of skin over the course of a treatment period. The effective amount of composition may vary based on the skin benefit desired by the user and/or the size of the treatment area. In some instances, the effective amount may range from 0.1 g to 5 g (e.g., 0.2 g to 4 g, 0.3 g to 2 g, or even 0.5 g to 1 g). The target portion of skin may be on a facial skin surface such as the forehead, perioral, chin, periorbital, nose, and/or cheek) or another part of the body (e.g., hands, arms, legs, back, chest). In some instances, the skin composition will be used before the post-acne mark forms in areas that are prone to acne lesions.

The skin care composition may be applied at least once a day, twice a day, or on a more frequent daily basis, during a treatment period. When applied twice daily, the first and second applications are separated by at least 1 to 12 hours. Typically, the composition is applied in the morning and/or at night before bed. The treatment period herein is ideally of sufficient time for skin care actives to improve the appearance of the skin. The treatment period may last for at least 1 week (e.g., about 2 weeks, 4 weeks, 8 weeks, 12 weeks, or even 16 weeks). In some instances, the treatment period will extend over multiple months (i.e., 3-12 months). In some instances, the composition may be applied most days of the week (e.g., at least 4, 5 or 6 days a week), at least once a day or even twice a day during a treatment period of at least 2 weeks, 4 weeks, 8 weeks, 12 weeks, or 16 weeks.

The composition can be intended for use at night and/or in the morning. It can be evenly massaged over the entire face (including or excluding the eye area) and/or neck. Alternatively, the composition may be applied locally to the target portion of skin in need of treatment and, if desired, to the surrounding skin. The product can be applied immediately after cleansing and/or before applying moisturizer and/or sunscreen.

The skin care composition can work on persistent marks, including post-acne marks, that are slow to fade. The composition was tested across skin tones and was formulated for all complexions, including complexions with a significant amount of melanin where post-acne marks and other dark marks can be persistent.

The composition can provide the following benefits:
Reduces the appearance of post acne marks
Provides visible recovery from post acne marks
Lightens the appearance of dark spots and discoloration
Fades hyperpigmentation to even complexion
Fades post acne mark faster
Prevents post acne marks
Prevents new post acne marks from forming
Provides faster spot recovery to restore natural skin tone
Provides faster results from the very first use
Returns post-acne marked skin to natural skin tone
Provides a stronger barrier for less noticeable post acne marks
Provides a strong barrier for optimum recovery
Hydrates skin to prevent darkest post acne marks
Repairs skin's barrier, restoring its nourished, natural state
Moisturizes skin for a balanced complexion
Increases cell turnover revealing brighter skin
Exfoliates away dead skin cells increasing cell turnover
Boosts cell turnover to fade dark marks
Provides protection for future damage
Calms skin, resetting skin's balance The step of applying the composition herein may be accomplished by localized application. In reference to application of the composition, the terms "localized," "local," or "locally" mean that the composition is delivered to the targeted area (e.g., a psoriatic plaque) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

Methods

HPLC

This method provides a way to determine the weight percentage of HCA and 4-vinylphenol (4-VP), respectively, in raw materials or finished products using high performance liquid chromatography ("HPLC"). This method may also be used to identify HCA and/or 4VP, by matching their wavelength spectrum and retention time to their respective known standards. The following instruments and materials are used in this method:

Instruments:
a gradient HPLC system that includes a gradient HPLC pump, liquid auto-sampler, UV detector (and diode array detector (DAD) for spectrum analysis), and a suitable computing integrator or computer data system (e.g., a Waters 2695 HPLC system from Waters Corporation or equivalent).
a Sum, 250 mm×4.6 mm ID HPLC column (e.g., a C18 column from Alltech Alltima).

Method:

Two mobile phases are used to create the gradient with a consistent flow rate of 1.0 mL/min. Mobile phase A consists of 0.5% acetic acid in purified water. Mobile phase B consists of 0.5% acetic acid in acetonitrile. The gradient is illustrated below in Table 1.

TABLE 1

| Analysis | Mobile Phase Composition (v/v) | |
|---|---|---|
| Time | % A | % B |
| 0.00 | 90 | 10 |
| 6.00 | 90 | 10 |
| 7.00 | 50 | 50 |
| 12.00 | 50 | 50 |
| 13.00 | 30 | 70 |
| 16.00 | 30 | 70 |

Figure 1B:
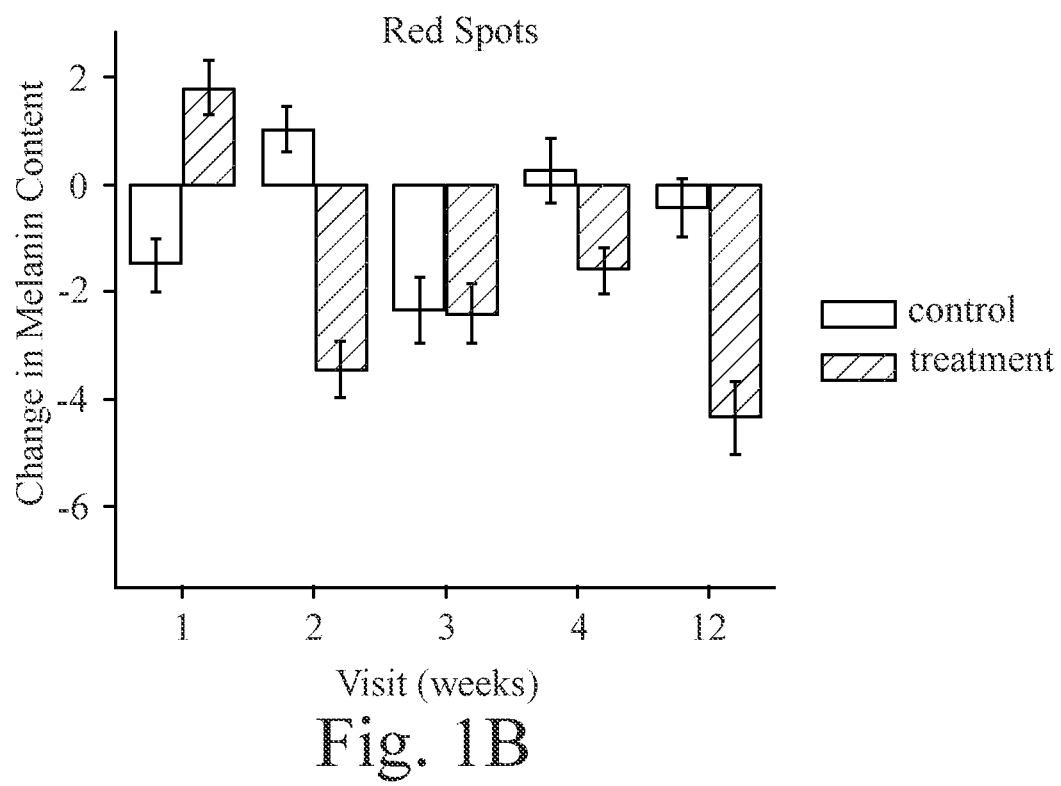
FIG. 1B shows the change in melanin content in red spots over 12 weeks for a Treatment Product and a Control Product.

The column temperature is 25 C. Data collection UV wavelength is 263 nm. The spectrum data between 190 nm and 400 nm are collected to identify the HCA and 4-VP. The retention time for HCA is 10.86 (±0.20) minutes, and the retention time for 4-VP is 14.60 (±0.20) minutes. The reference spectrum for HCA and 4-VP are shown in FIGS. 1A and 1B, respectively.

Calculations

1. Calculation of Wt % of HCA in Finished Product Samples $$HCA\ Wt\ \% = \frac{A \times M \times P \times 100}{B \times W}$$

A=Peak area ratio of HCA:Internal Standard in sample
B=Peak Area ratio of HCA:Internal Standard in Calibration Standard
M=Mass of HCA in mg, in Calibration Standard (~50 mg/50 mL×3 mL)
W=Sample weight in mg
P=Purity of HCA in decimal 2. Calculation of wt % of 4-VP in Finished Product Samples $$4VP\ Wt\ \% = \frac{a \times m \times p \times 100}{b \times w}$$

a=Peak area ratio of 4-VP:Internal Standard in sample
b=Peak area ratio of 4-VP:Internal Standard in Calibration Standard
m=Mass of 4-VP in mg, in Calibration Standard (~150 mg/100 mL×1 mL)
W=Sample weight in mg
p=Purity of 4-VP in decimal HCA Crystallization This method provides a way to determine HCA solubility in a composition by observing HCA crystals in situ. The method involves cycling the temperature of a test sample between freezing and thawing to imitate environmental conditions experienced by a skin care composition at an accelerated rate. This type of accelerated aging is commonly used in cosmetic product stability testing. HCA crystals can be detected using conventional means such as visual observation and microscopy.

A bulk sample of at least 10 g (e.g., 20 g-60 g) of the composition to be tested is placed in a suitable container that enables visual observation of the test sample (e.g., transparent plastic or glass jar). The test sample is subjected to 1 month of freeze/thaw temperature cycling to simulate environmental conditions that a skin care product may experience during shipping and storage. This is sometimes referred to as accelerated aging. The temperature cycling involves a 1-week freeze cycle at −7° C., followed by a 1-week thaw cycle at 25° C., and then repeating this freeze/cycle for a total temperature cycling time of 1 month.

Upon completion of the accelerated aging process (i.e., 1 month of temperature cycling), transparent test samples are visually inspected in-situ in the transparent container to determine if HCA crystallization/precipitation occurred. For opaque and translucent samples, the entire test sample is removed from the container and transferred to a suitable transparent substrate (e.g., plastic film or glass plate) and formed into a thin film of no more than 1 mm thickness. The sample is covered with a second transparent substrate to inhibit the loss of volatile ingredients during inspection. A light source (e.g., LED lamp or the like) is used to backlight the sample to aid in visual inspection. HCA crystals will generally appear as a precipitate in the composition visible to the naked eye when observed by someone with 20/20 vision from 45 cm away. Any precipitate identified during visual observation is further evaluated using a microscope capable of providing fluorescent birefringence observation with cross-polarized light to identify anisotropic crystals. Any anisotropic crystal that has a longest dimension of greater than 0.1 mm is identified as an HCA crystal and the total number of HCA crystals is recorded. A test sample that contains no more than 1 HCA crystal is considered to be "free of HCA crystals" and is recorded as a "pass." A test sample that contains more than 1 HCA crystal, is recorded as a "fail."

While not required, fourier-transform infrared spectroscopy (FTIR) can be used to confirm that the HCA crystal or co-crystal contains the appropriate hydroxycinnamic acid structure. FTIR spectroscopy techniques are well-known in the art. See, U.S. Pat. No. 10,912,857, US2020/0000697, and Fourier Transform Infrared Spectroscopy in Colloid and Interface Science, D. R. Scheuing, Ed., American Chemical Society, 225, 1991.

Rheology

This method provides a way to measure the dynamic viscosity of a composition or material using a BROOKFIELD brand viscometer (e.g., model DV2T or equivalent) and a suitable spindle (e.g., RV4 or equivalent) according to the manufacturer's instructions. It is to be appreciated that the skilled artisan will be able to select the appropriate spindle in accordance with the manufacturer's recommendation. After calibrating the viscometer, the spindle is immersed into a sufficient quantity of test sample (e.g., enough to immerse the spindle up to the immersion mark on the spindle shaft). Set the spindle rotation speed to 5 rpm, and then start the viscometer. Allow time for the indicated viscosity reading to stabilize (approximately 10-30 seconds). After the reading stabilizes, take 5 readings at 10 second intervals. Calculate the viscosity as the average of the 5 readings.

EXAMPLES

The following data and examples are provided to help illustrate the skincare compositions and method described herein. The exemplified compositions and methods are given solely for the purpose of illustration and are not to be construed as limitations of the present disclosure, as many variations thereof are possible without departing from the spirit and scope of the disclosure. All parts, percentages, and ratios herein are by weight unless otherwise specified.

Example 1: Clinical Study

A randomized, double-blind clinical study was conducted to evaluate the potential benefit of compositions with niacinamide, HCA, and a low pH focused on reducing the appearance of spots, post acne marks. 62 female subjects (age range 18 to 45, mean: 35.79, standard deviation: 5.42) with wide range of skin tones (measured by Individual Typology Angle—ITA (reference Del Bino S, Bernerd F, British Journal of Dermatology (2013) 169 (Suppl. 3), pp 33-40), ITA range −66.5 to +46.3. mean: 13.88, standard deviation: 27.46) who had a history of post acne marks were recruited. The Treatment Product, as shown in Table 2 below, contained 2% niacinamide and 0.5% HCA as the active ingredients and the composition had a pH of 3.8. The Treatment Product was compared a Control Product, as shown in Table 2 below, which did not have the active ingredients (HCA and niacinamide) and had a pH of 5.0. Other ingredient differences include a small amount of humectant in the Treatment Product to help with treatment tolerability and preservatives, pH adjusters, and emulsifying agents to help keep the compositions stable. It is believed that the active ingredients are what made the difference in product performance.

TABLE 2

| Component | Treatment Product % | Control Product % |
| --- | --- | --- |
| Water | qs | qs |
| Glycerin | 3.00 | 3.00 |
| Dimethicone 5 cSt | 4.00 | 4.00 |
| Niacinamide | 2.00 | |
| Lactic acid | 1.80 | |
| Sodium lactate | 1.30 | |
| Polyacrylate crosspolymer-6 [1] | 1.10 | 0.50 |
| D-Panthenol | 0.50 | |
| Disodium EDTA | 0.10 | 0.10 |
| PEG-11 methyl ether dimethicone [3] | 0.10 | 0.10 |
| Trehalose | 0.10 | |
| Sodium benzoate | 0.05 | 0.05 |
| Sodium sulfite | 0.05 | |
| 4-HCA [4] | 0.50 | |
| PEG-4 [4] | 2.83 | |
| Isopropyl lauroyl sarcosinate [5] | 4.00 | 4.00 |
| Pentylene glycol | 3.00 | 3.00 |
| Sucrose Dilaurate | 0.30 | |
| Hydroxy acetophenone | | 0.25 |
| Phenoxyethanol | | 0.25 |
| Aminomethyl Propanol | | 0.001 |
| NaOH | * | * |
| HCl | * | * |
| pH | 3.8 | 5.0 |

After a one-week preconditioning period, subjects applied the Treatment Product and the Control Product on randomized split-face for 12 weeks period. Clinical images were taken at Baseline, week 1, week 2, week 3, week 4, week 8, and week 12 using Visia®-CR4 and OLÉ® Imager (Canfield Scientific, Inc., New Jersey, USA) in a controlled humidity/temperature lab (temperature 70° F.±2° F., relative humidity 30-45%). Subjects acclimated in the lab for at least 30 mins prior to clinical measurements. 58 subjects completed the study.

Image analysis was used to track individual spots on the face. The image analysis method broadly categorizes spots into red spots and brown spots based on the dominant chromophore of the spots. It characterizes the dynamic changes of chromophores of each spot, in particular the amount of melanin and hemoglobin, and thereby evaluates the efficacy of the treatment. The error bars in FIGS. 1A-D represent the one standard error (SE).

Figure 1C:
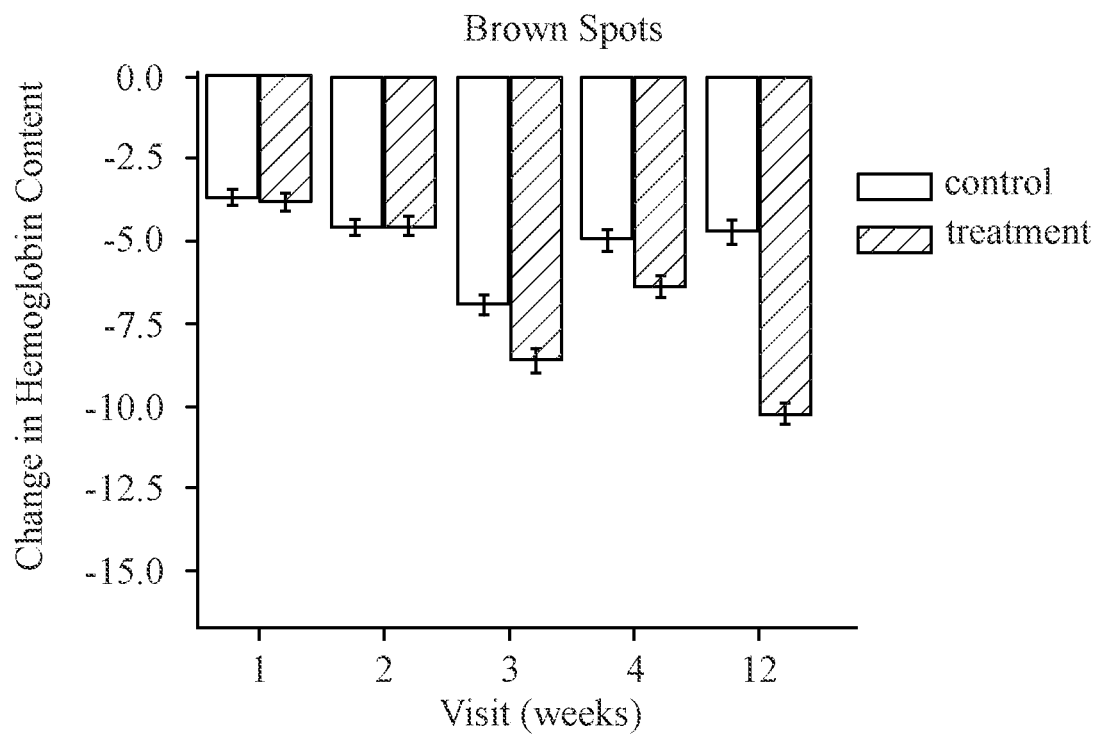
FIG. 1C shows the change in hemoglobin content in brown spots over 12 weeks for a Treatment Product and a Control Product.

FIGS. 1A and 1C show the change in melanin and hemoglobin, respectively, for spots that are brown, meaning that they have more melanin as compared to hemoglobin, for both the Treatment Product and the Control Product.

Figure 1D:
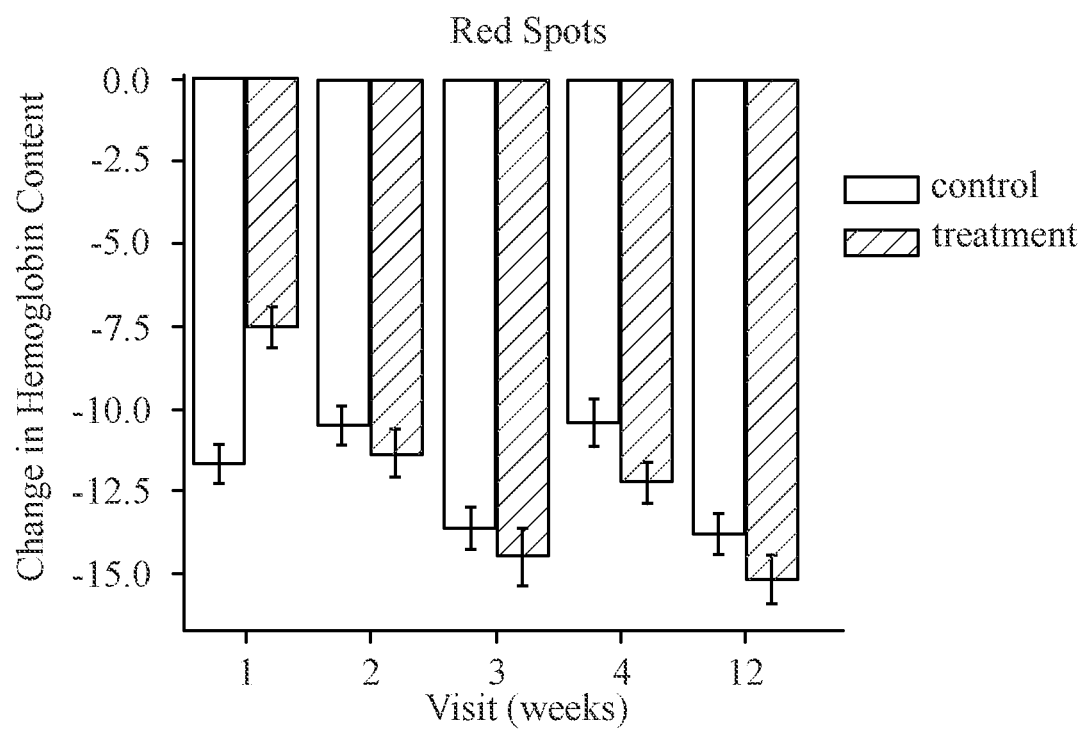
FIG. 1D shows the change in hemoglobin content in brown spots over 12 weeks for a Treatment Product and a Control Product.

FIGS. 1B and 1D show the change in melanin and hemoglobin, respectively, for spots that are red, meaning that they have more hemoglobin as compared to melanin, for both the Treatment Product and the Control Product.

FIGS. 1A and 1B show that the Treatment Product significantly reduces the melanin content in both red and brown spots after two weeks. There was little change in the Control Product after 12 weeks, which shows that melanin spots are difficult to remove without treatment.

FIGS. 1C and 1D show that the Treatment Product reduces hemoglobin content in both brown and red spots. However, the change looks less significant in the graphs in FIGS. 1C and 1D, as compared to the reduction in melanin shown in FIGS. 1A and 1B. However, as discussed hereafter, and shown in FIGS. 2A-D, the rate of change of both melanin and hemoglobin is greatly improved with the Treatment Product as compared to the Control Product. Furthermore, the hemoglobin in the brown and red spots also improved over the 12 weeks with the Control Product, however, FIGS. 1C and 1D show that the improvement is less dramatic, as compared to the Treatment Product.

Since these spots can be considered dynamic, chromophore change with time can be fitted with a regression model to model the dynamic nature of each and every spot. The rate of change is represented by the gradient of the regression fit. We built a machine learning model and leverage explainable AI (XAI) approach, as described below, to elucidate the impact of treatment on rate of the improvement (measured by the gradient of the regression fit). Results are shown in FIGS. 2A-D. The error bar represents one SE. In these Figures, the y-axis shows the Shap values, which describes the impact of the variable on the chromophore. Mean change of chromophore change is given as a base value. Contrast of Shap values between the Treatment Product (effect magnitude and trend) and the Control Product can be used determine the impact of the product.

A Gradient booster (Chen T and Guestrin C, XGBoost: A Scalable Tree Boosting System, arXiv:1603.02754, 2016) machine learning model was built to predict the rate of change of spot chromophores using age, ITA, spot count, BMI and treatment as predictor variables. Since machine learning models are inherently opaque, Shapley based explainable AI approach (Lundberg S and Lee S, A Unified Approach to Interpreting Model Predictions, arXiv: 1705.07874, 2017) was used to evaluate the impact of each predictor variables. The Shap values describe the impact of the variable on the rate of chromophore change. Mean change of chromophore change is given as a base value in FIGS. 2A-D and comparing the Shap values between the Treatment Product (effect magnitude and trend) and the Control Product can be used to determine the impact of each product.

Figure 2A:
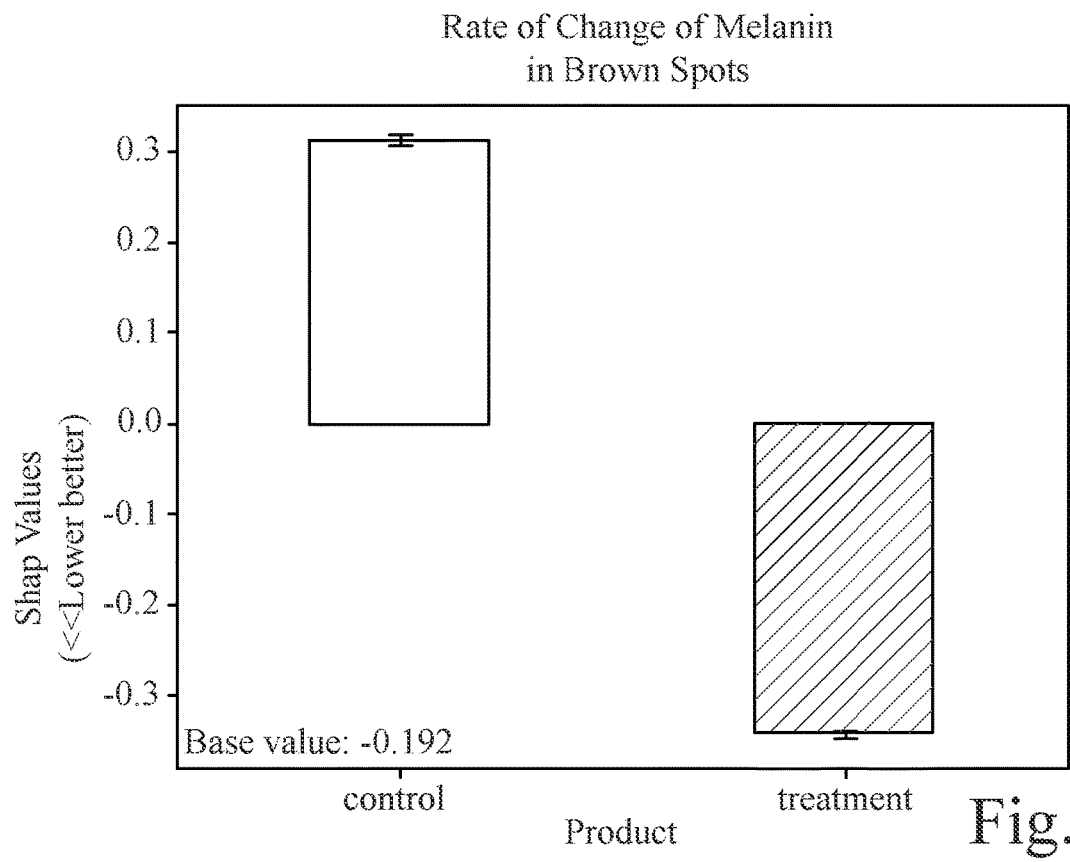
FIG. 2A shows the rate of change of melanin in brown spots.
Figure 2B:
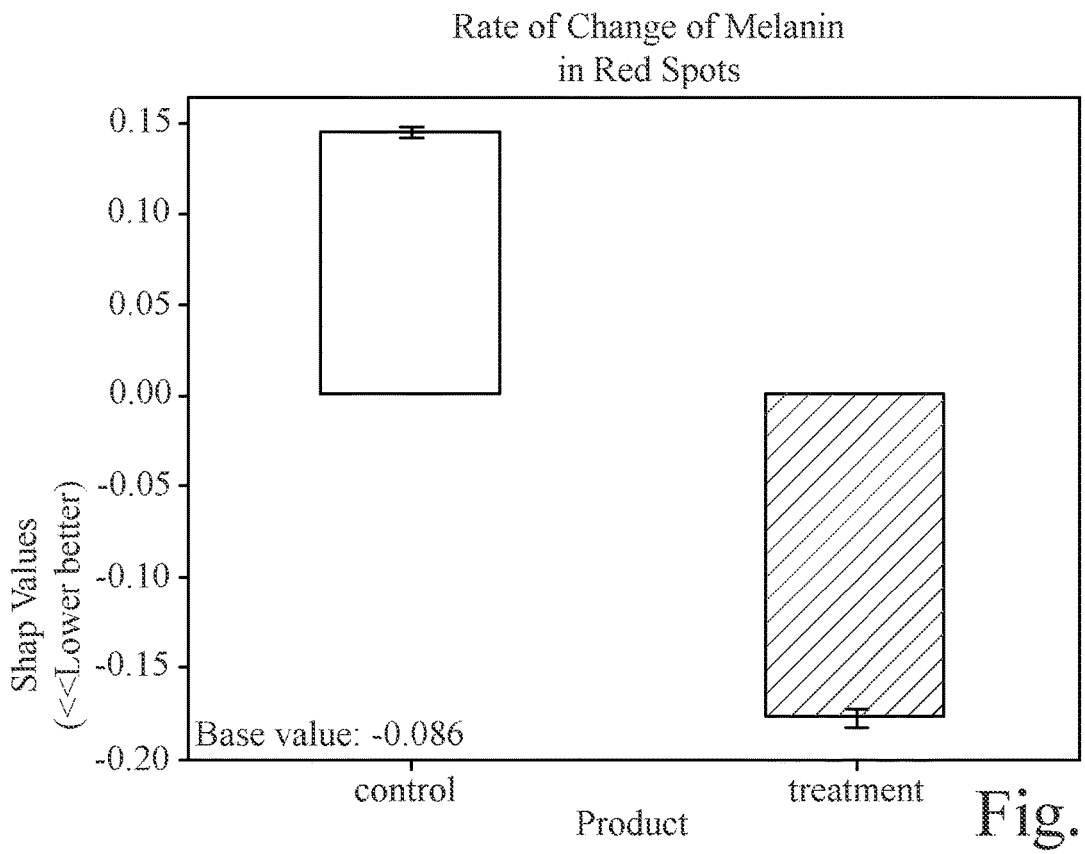
FIG. 2B shows the rate of change of melanin in red spots.

FIG. 2A shows the rate of change of melanin in brown spots and FIG. 2B shows the rate of change of melanin in red spots. The negative shap values for both Treatment Products indicate that the rate of change is significant for the Treatment Product, as compared to the Control Product.

Figure 2C:
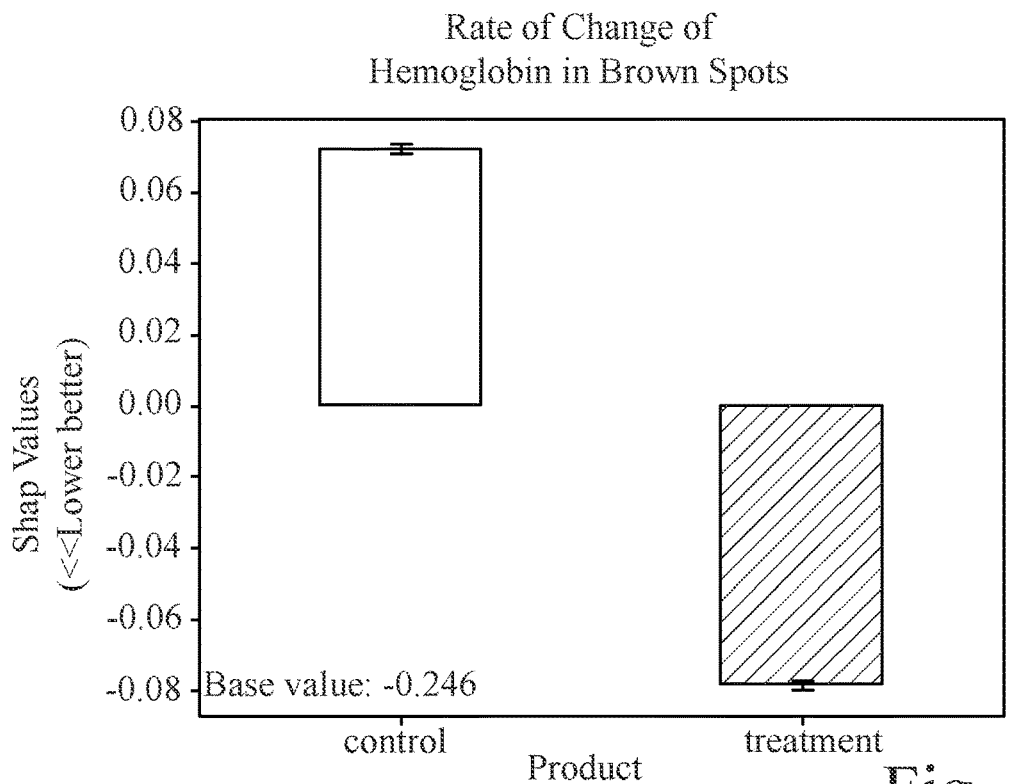
FIG. 2C shows the rate of change of hemoglobin in brown spots.
Figure 2D:
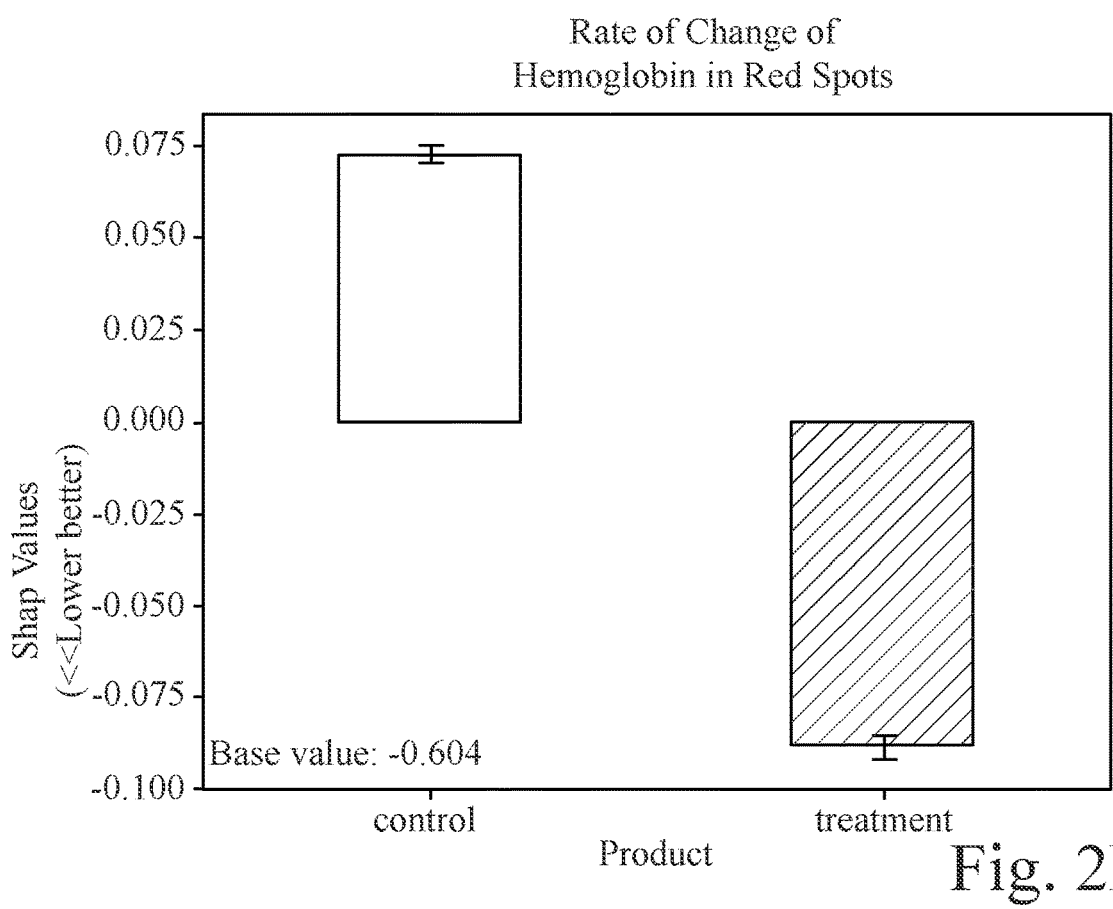
FIG. 2D shows the rate of change of hemoglobin in red spots.

FIG. 2C shows the rate of change of hemoglobin in brown spots and FIG. 2D shows the rate of change of hemoglobin in red spots. The negative shap values for both Treatment Products indicate that the rate of change is significant for the Treatment Product, as compared to the Control Product.

Example 2: Low-pH Skin Care Composition Examples

Table 3 and Table 4 below provides examples of low-pH skin care compositions that correspond to various aspects of the invention. The compositions can be prepared using conventional methods of making skin care compositions. Such methods typically involve mixing of the ingredients in one or more steps to a relatively uniform state, with or without heating, cooling, application of vacuum, and the like. All exemplified amounts exclude minor materials such as diluents, preservatives, color solutions, feel modifying powders and elastomers, etc., that may be present in a commercial product unless otherwise specified. HCA may be added as a solid form and solubilized in-situ, dissolved as a premix, or supplied as a pre-dispered raw material. A pre-dispersed 15% solution of 4-HCA in PEG-4 (Lipobrite® from Vantage) is used for certain examples. For examples containing Lipobrite®, the 4-HCA and PEG-4 constituent levels are listed individually for clarity, with a superscript to denote the Lipobrite® raw material. The total Lipobrite® material added is the sum of the 4-HCA and PEG-4 constituents listed. All other materials are listed 'as is' from the suppliers.

Emulsions are prepared by first mixing the aqueous phase materials separately from the oil and/or silicone phase materials and then combining the two phases as appropriate to yield the desired continuous phase. In some aspects, the exemplary compositions can be made by blending the aqueous phase components with a suitable mixer (e.g., IKA RW20 or equivalent) until all materials are dissolved and homogeneous. When present, the optional polymer thickener may be hydrated by slowing adding the thickener directly into a water phase while stirring and continued mixing until homogeneous. The 4-HCA, polar emollient, and glycol co-solvent may be added together in a separate pre-mix container and mixed until fully dissolved and uniform. The HCA premix can then be added to the main mix container and further mixed until homogeneous. The formula can be milled using a suitable mixer (e.g., IKA Ultra Turrax T-25 or equivalent) to reduce the emulsion particle size until a target viscosity is reached and uniform composition is achieved. The temperature may be adjusted as needed to control the speed of the process and/or achieve a homogenous final product.

TABLE 3

| Component | A | B | C | D | E | F | G |
|---|---|---|---|---|---|---|---|
| | wt. % | | | | | | |
| Water | qs | qs | qs | qs | qs | qs | qs |
| Glycerin | 7.00 | 3.00 | 3.00 | 3.00 | 3.00 | 3.00 | 3.00 |
| Dimethicone 5 cSt | — | — | 2.00 | 2.00 | 2.00 | 2.00 | 2.00 |
| Niacinamide | 2.00 | 2.00 | 2.00 | 2.00 | 2.00 | 5.00 | 2.00 |
| Lactic acid | 1.80 | 1.80 | 1.80 | 1.80 | 1.80 | 1.80 | 1.80 |
| Sodium lactate | 1.30 | 1.30 | 1.30 | 1.30 | 1.30 | 1.30 | 1.30 |
| Polyacrylate crosspolymer-6[1] | — | — | 1.25 | 1.25 | 1.25 | 1.25 | 1.25 |
| Sodium polyacryloyldimethyl taurate[2] | 1.25 | 1.25 | — | — | — | — | — |
| D-Panthenol | 0.50 | 0.50 | 0.50 | 0.50 | 0.50 | 0.50 | 0.50 |
| Di sodium EDTA | 0.10 | 0.10 | 0.10 | 0.10 | 0.10 | 0.10 | 0.10 |
| PEG-11 methyl ether dimethicone[3] | — | — | 0.10 | 0.10 | 0.10 | 0.10 | 0.10 |
| Trehalose | — | — | 0.50 | 0.50 | 0.50 | 0.50 | 0.50 |
| Sodium benzoate | 0.05 | 0.05 | 0.05 | 0.05 | 0.05 | 0.05 | 0.05 |
| Sodium sulfite | — | 0.05 | 0.05 | 0.05 | 0.05 | 0.05 | 0.05 |
| 4-HCA[4] | 0.0001 | 1.00 | 0.50 | 0.25 | 0.10 | 1.00 | 0.30 |
| PEG-4[4] | 0.00057 | 5.67 | 2.83 | 1.42 | 0.57 | 5.67 | 1.7 |
| Isopropyl lauroyl sarcosinate[5] | 0.10 | 5.00 | 4.00 | 3.00 | 1.00 | 5.00 | 1.00 |
| Pentylene glycol | 0.10 | 3.00 | 3.00 | 3.00 | 3.00 | 3.00 | 3.00 |
| Propylene glycol | — | 5.00 | — | — | — | 5.00 | 5.00 |
| Dipropylene glycol | — | 4.00 | — | — | — | 4.00 | 4.00 |
| Ethoxy diglycol | — | 2.60 | — | — | — | 2.60 | — |
| Isohexadecane | 3.00 | 3.00 | — | — | — | — | — |
| Isopropyl isostearate | 1.50 | 1.50 | — | — | — | — | — |
| Cetearyl glucoside and cetearyl | 0.50 | 0.50 | — | — | — | — | — |
| Behenyl Alcohol | 0.70 | 0.70 | — | — | — | — | — |
| Stearyl Alcohol | 1.20 | 1.20 | — | — | — | — | — |
| Cetyl Alcohol | 0.90 | 0.90 | — | — | — | — | — |
| PEG-100 Stearate | 0.10 | 0.10 | — | — | — | — | — |
| Stearic Acid | 0.10 | 0.10 | — | — | — | — | — |
| Dimethicone and dimethiconol[6] | 1.00 | 1.00 | — | — | — | — | — |
| Palmitoyl pentapeptide-4[7] | 0.50 | 0.50 | — | — | — | — | — |
| Sucrose Dilaurate | | | | | | | |
| Hydroxy acetophenone | | | | | | | |
| Phenoxyethanol | | | | | | | |
| Aminomethyl Propanol | | | | | | | |
| NaOH | * | * | * | * | * | * | * |
| HCl | * | * | * | * | * | * | * |
| pH | 4.0 | 4.0 | 4.0 | 4.0 | 3.0 | 5.0 | 3.8 |

TABLE 4

| | H | I | J | K | L | M | N |
|---|---|---|---|---|---|---|---|
| | wt. % | | | | | | |
| Water | qs | qs | qs | qs | qs | qs | qs |
| Glycerin | 3.00 | 3.00 | 3.00 | 7.00 | 3.00 | 3.00 | 3.00 |
| Dimethicone 5 cSt | 2.00 | 2.00 | — | — | 2.00 | 2.00 | 2.00 |
| Niacinamide | 2.00 | 0.50 | 2.00 | 0.10 | 0.50 | 0.50 | 2.00 |
| Lactic acid | 1.80 | 1.80 | 1.80 | 1.80 | 1.80 | 1.80 | 1.80 |
| Sodium lactate | 1.30 | 1.30 | 1.30 | 1.30 | 1.30 | 1.30 | 1.30 |
| Polyacrylate crosspolymer-6[1] | 1.20 | 1.20 | 1.20 | 1.25 | 1.20 | 1.20 | 1.20 |
| Sodium polyacryloyldimethyl taurate[2] | — | — | — | — | — | — | — |
| Panthenol | 0.50 | 0.50 | 0.50 | 0.50 | 0.50 | 0.50 | 0.50 |
| Di sodium EDTA | 0.10 | 0.10 | 0.10 | 0.10 | 0.10 | 0.10 | 0.10 |

TABLE 4-continued

| | H | I | J | K wt. % | L | M | N |
|---|---|---|---|---|---|---|---|
| PEG-11 methyl ether dimethicone³ | 0.10 | 0.10 | 0.10 | — | 0.10 | 0.10 | 0.10 |
| Trehalose | 0.10 | 0.10 | 0.10 | 0.10 | 0.10 | 0.10 | 0.10 |
| Sodium benzoate | 0.05 | 0.05 | 0.05 | 0.05 | 0.05 | 0.05 | 0.05 |
| Ferulic acid | 0.25 | 0.25 | 0.25 | — | — | — | — |
| 4-HCA⁴ | 0.25 | 0.25 | 0.25 | 0.10 | 0.5 | 0.5 | 0.5 |
| PEG-4⁴ | 1.42 | 1.42 | 1.42 | 0.57 | 2.83 | 2.83 | 2.83 |
| Isopropyl lauroyl sarcosinate⁵ | 4.00 | 4.00 | 4.00 | 1.00 | 1.00 | 3.00 | 1.00 |
| Pentylene glycol | 3.00 | 3.00 | — | 3.00 | 3.00 | 3.00 | 3.00 |
| Propylene glycol | — | — | — | — | 5.00 | 5.00 | 5.00 |
| Dipropylene glycol | — | — | — | — | 4.00 | 4.00 | 4.00 |
| Isohexadecane | — | — | 3.00 | 3.00 | — | — | — |
| Isopropyl isostearate | — | — | 1.50 | 1.50 | — | — | — |
| Cetearyl glucoside and cetearyl | — | — | 0.50 | 0.50 | — | — | — |
| Behenyl alcohol | — | — | 0.70 | 0.70 | — | — | — |
| Stearyl alcohol | — | — | 1.20 | 1.20 | — | — | — |
| Cetyl alcohol | — | — | 0.90 | 0.90 | — | — | — |
| PEG-100 stearate | — | — | 0.10 | 0.10 | — | — | — |
| Stearic acid | — | — | 0.10 | 0.10 | — | — | — |
| Dimethicone and dimethiconol⁶ | — | — | 1.00 | 1.00 | 1.00 | — | — |
| Palmitoyl pentapeptide-4⁷ | — | — | 0.5 | 0.50 | — | — | — |
| NaOH | * | * | * | * | * | * | * |
| HCl | * | * | * | * | * | * | * |
| pH | 4.0 | 5.0 | 4.0 | 2.5 | 3.0 | 2.5 | 4.0 |

Tradenames and Suppliers for Table 2 to Table 4:
[1] SEPIMAX ZEN available from Seppic
[2] ARISTOFLEX SILK available from Clariant
[3] KF-6011 available from Shin-Etsu
[4] LIPOBRITE from Vantage (15% 4-HCA, 85% PEG-4)
[5] Eldew SL-205 from Ajinomoto OmniChem
[6] DC-1503 from Dow Corning
[7] Ferulic Acid from Sigma Aldrich
[8] PROMATRIXYL from Croda
* pH adjustment as necessary The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

The following paragraphs MUST be inserted when preparing U.S. Provisional, Perfected Filings of U.S. Provisionals and 12 month U.S. non-design filings.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of reducing the appearance of post-acne marks comprising:
   a. identifying a target portion of skin comprising a post-acne mark;
   b. applying an effective amount of a skin care composition to the target portion of skin over the course of a treatment period; wherein the skin care composition comprises:
      i. about 0.1% to about 10% of a vitamin $B_3$ compound;
      ii. about 0.1% to about 10% of a hydroxycinnamic acid;
      iii. water;
      iv. about 0.1% to about 5% of a polar emollient; and
      v. a co-solvent with a Hansen solubility parameter distance of less than 15 from the hydroxycinnamic acid;
   wherein a pH of the composition is 5.0 or less;
   wherein the composition is free of hydroxycinnamic acid crystals.

2. The method of claim 1, wherein a weight ratio between the hydroxycinnamic acid and the polar emollient is from about 1:1 to about 1:10.

3. The method of claim 1, wherein the composition comprises less than 20% of the co-solvent.

4. The method of claim 3, wherein the co-solvent is a glycol chosen from propylene glycol, dipropylene glycol, butylene glycol, pentylene glycol, hexylene glycol, ethoxydiglycol, C2-C6 polyethene glycols, or mixtures thereof.

5. The method of claim 1, wherein the vitamin $B_3$ compound is niacinamide.

6. The method of claim 1, where in the composition further comprises a polymer thickener.

7. The method of claim 6, wherein the polymer thickener comprises polyacrylate crosspolymer-6.

8. The method of claim 1, wherein the composition further comprises about 0.001% to about 5% by weight of an antioxidant.

9. The method of claim 8, wherein the antioxidant is chosen from sodium sulfite, sodium bisulfite, sodium metabisulfite, or mixtures thereof.

10. The method of claim 1, wherein the pH is from about 2.0 to about 4.5.

11. The method of claim 1, wherein the hydroxycinnamic acid comprises p-coumaric acid.

12. The method of claim 1, wherein the hydroxycinnamic acid comprises ferulic acid.

13. A method of lightening the appearance of dark spots and discoloration comprising:
   a. identifying a target portion of skin comprising a post-acne mark;
   b. applying an effective amount of a skin care composition to the target portion of skin over the course of a treatment period; wherein the skin care composition comprises:
      i. niacinamide;
      ii. coumaric acid;
      iii. isopropyl lauroyl sarcosinate; and
      iv. pentylene glycol;
         wherein the composition comprises a pH of less than 5.0, a viscosity of about 1 cP to about 15,000 cP at 25° C., and is free of coumaric acid crystals.

14. The method of claim 13, wherein the composition further comprises sodium sulfite.

15. A method of fading post-acne marks faster and/or preventing appearance of new post-acne marks comprising:
   a. identifying a target portion of skin comprising a post-acne mark;
   b. applying an effective amount of a skin care composition to the target portion of skin over the course of a treatment period; wherein the skin care composition comprises:
      i. a vitamin $B_3$ compound;
      ii. a hydroxycinnamic acid (HCA);
      iii. a polar emollient;
      iv. a co-solvent with a Hansen solubility parameter distance of less than 15 from the hydroxycinnamic acid; and
      v. water;
         wherein the pH of the composition is less than 5.0 and the composition exhibits less than 25% HCA degradation according to the HPLC Method described herein.

16. The method of claim 15, wherein the composition comprises less than 1000 parts-per-million of 4-vinylphenol.

17. The method of claim 15, wherein the composition exhibits less than about 10% HCA degradation according to the HPLC Method described herein.

18. The method of claim 1, wherein the polar emollient is an amino acid ester derivative.

\* \* \* \* \*